(12) United States Patent
Nwachukwu et al.

(10) Patent No.: US 10,632,221 B2
(45) Date of Patent: *Apr. 28, 2020

(54) LONG LASTING AND STABLE FRESHENING COMPOSITIONS AND METHODS OF FRESHENING THE AIR

(71) Applicant: The Procter & Gamble Company, Cincinnati, OH (US)

(72) Inventors: Chisomaga Ugochi Nwachukwu, Cincinnati, OH (US); Judith Ann Hollingshead, Batavia, OH (US); Zaiyou Liu, West Chester, OH (US); George Kavin Morgan, III, Hamilton, OH (US); Christine Marie Readnour, Ft. Mitchell, KY (US); Laura Jane Zielewicz, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/469,617

(22) Filed: Mar. 27, 2017

(65) Prior Publication Data

US 2017/0274111 A1    Sep. 28, 2017

Related U.S. Application Data

(60) Provisional application No. 62/313,833, filed on Mar. 28, 2016.

(51) Int. Cl.
*A61L 9/14* (2006.01)
*C11B 9/00* (2006.01)
(Continued)

(52) U.S. Cl.
CPC ...... *A61L 9/14* (2013.01); *A61L 9/01* (2013.01); *C11B 9/0003* (2013.01);
(Continued)

(58) Field of Classification Search
CPC .................................................. A61L 9/14
See application file for complete search history.

(56) References Cited

U.S. PATENT DOCUMENTS 3,213,129 A    10/1965 Peter
3,979,306 A    9/1976 Arai
(Continued)

FOREIGN PATENT DOCUMENTS

WO    WO 2004/105713 A1    12/2004
WO    WO 2012/113746 A1    8/2012
(Continued)

OTHER PUBLICATIONS

PCT Search Report PCT/US2017/024230; P&G Case 14261M; Dated Mar. 27, 2017; 15 Pages.
(Continued)

*Primary Examiner* — Arrie L Reuther
(74) *Attorney, Agent, or Firm* — Abbey A. Lopez

(57) ABSTRACT

A freshening composition is provided. The freshening composition includes about 0.02 wt. % to about 1.0 wt. %, based on the weight of the composition, of a sulfur-containing pro-perfume. The freshening composition further includes about 0.2 wt. % to about 1.4 wt. %, based on the weight of the composition, of a perfume mixture, the perfume mixture comprising at least one perfume material selected from the group consisting of: 3-(1,3-Benzodioxol-5-yl)-2-methylpropanal, canthoxal, vanillin, ethyl vanillin, citral, ligustral, cinnamic aldehydes, and combinations thereof. The freshening composition also includes a carrier.

10 Claims, 3 Drawing Sheets

(51) Int. Cl.
  *A61L 9/01* (2006.01)
  *A61L 9/04* (2006.01)
(52) U.S. Cl.
  CPC .......... *C11B 9/0015* (2013.01); *C11B 9/0061* (2013.01); *C11B 9/0076* (2013.01); *A61L 9/04* (2013.01)

(56) References Cited

U.S. PATENT DOCUMENTS

| | | | |
|---|---|---|---|
| 4,854,333 A | 8/1989 | Inman | |
| 5,518,644 A | 5/1996 | De Buzzaccarini | |
| 5,609,856 A | 3/1997 | Dubief | |
| 5,609,861 A | 3/1997 | Dubief | |
| 7,030,079 B1 * | 4/2006 | Apel | A61K 8/31 512/1 |
| 7,399,318 B2 | 7/2008 | Nagano | |
| 2002/0174491 A1 | 11/2002 | Fischer | |
| 2008/0305976 A1 | 12/2008 | Turin | |
| 2009/0092561 A1 | 4/2009 | Lupia | |
| 2015/0217015 A1 * | 8/2015 | Williams | A61L 9/01 424/76.21 |
| 2015/0335778 A1 | 11/2015 | Nwachukwu et al. | |
| 2016/0222327 A1 | 8/2016 | Herrmann | |

FOREIGN PATENT DOCUMENTS

| | | | |
|---|---|---|---|
| WO | WO 2014/176392 A1 | 10/2014 | |
| WO | WO-2015032885 A1 * | 3/2015 | ........... C11B 9/0003 |
| WO | WO 2015/119813 A1 | 8/2015 | |
| WO | WO2015119813 A1 | 8/2015 | |
| WO | WO2016135193 A1 | 9/2016 | |
| WO | WO2016205029 A1 | 12/2016 | |
| WO | WO2017172567 A1 | 10/2017 | |
| WO | WO2017172568 A1 | 10/2017 | |

OTHER PUBLICATIONS

PCT Search Report PCT/US2017/024229; P&G Case 14262M; Dated Mar. 27, 2017; 15 Pages.
U.S. Appl. No. 15/469,615, filed Mar. 27, 2017, Nwachukwu, et al.
Umberto Maddalena et al: "ThioetherProfragrances: Parameters Influencing thePerformance of Precursor-Based FragranceDe 1 i very in Funct i ona 1 Perfumery",Chemistry & Biodiversity,vol. 11, No. 11,Nov. 1, 2014 (Nov. 1, 2014), pp. 1700-1733.
All Office Action for P&G Case 14261M, U.S. Appl. No. 15/469,615.

* cited by examiner

LONG LASTING AND STABLE FRESHENING COMPOSITIONS AND METHODS OF FRESHENING THE AIR

FIELD

The present disclosure relates to stable, long-lasting freshening products including freshening compositions that comprise sulfur containing pro-perfumes and methods of freshening the air with the freshening compositions.

BACKGROUND

Freshening compositions for reducing or masking malodors with scent on inanimate surfaces such as fabrics and in air are currently available and are described in the patent literature. Compositions that are capable of delivering long-lasting scent on inanimate surfaces and in the air also exist. Some compositions contain high amounts of perfume in order to provide long-lasting scent or freshness into the air. However, such compositions may deliver an overwhelming amount of scent into the air after the product is initially delivered to the air.

Moreover, it may be important that the freshening compositions have a relatively long shelf life so that the compositions are effective at freshening the air for several months after the product is manufactured. Some freshening compositions contain active ingredients used to counteract malodors. However, such long-lasting compositions that have actives for reducing malodor may be unstable or susceptible to reacting with other ingredients of the composition. This may be especially true for aqueous compositions that may be more susceptible to oxidation.

As such, it would be beneficial to provide a freshening composition that provides long-lasting freshness to the air while delivering a relatively consistent scent over time.

Moreover, it would be beneficial to deliver a long-lasting freshness to the air with a freshening composition that has a relatively long shelf-life.

SUMMARY

A. A freshening composition comprising:
   about 0.02 wt. % to about 1.0 wt. %, based on the weight of the composition, of a sulfur-containing pro-perfume;
   about 0.2 wt. % to about 1.4 wt. %, based on the weight of the composition, of a perfume mixture, the perfume mixture comprising at least one perfume material selected from the group consisting of: 3-(1,3-Benzodioxol-5-yl)-2-methylpropanal, canthoxal, vanillin, ethyl vanillin, citral, ligustral, cinnamic aldehydes, and combinations thereof; and
   a carrier.
B. The freshening composition of Paragraph A, wherein the freshening composition comprises a pH in the range of about 3 to about 8.5, more preferably in the range of about 4 to about 6.5.
C. The freshening composition according to any of Paragraphs A-B further comprising a carboxylic acid, preferably the carboxylic acid is citric acid or polyacrylic acid.
D. The freshening composition according to Paragraphs A-C further comprising a secondary or tertiary amine, wherein the freshening composition comprises a weight ratio of carboxylic acid to secondary or tertiary amine of equal to or greater than 3:1.
E. The freshening composition of Paragraph A-D, wherein the perfume mixture further comprises dimethyl anthranilate.
F. The freshening composition according to any of Paragraphs A-E, wherein the freshening composition comprises a weight ratio of perfume mixture to sulfur-containing pro-perfume of about 3:1 to about 35:1, more preferably about 8:1 to about 25:1, most preferably about 10:1 to about 20:1, by weight of the freshening composition.
G. The freshening composition according to any of Paragraphs A-F, wherein the sulfur-containing pro-perfume is present at a level of about 0.02 wt. % to about 1.0 wt. %, preferably about 0.02 wt. % to about 0.8 wt. %, more preferably about 0.03 wt. % to about 0.3 wt. %, most preferably about 0.03 wt % to about 0.09 wt %, by weight of the freshening composition.
H. The freshening composition according to any of Paragraphs A-G, wherein the sulfur-containing pro-perfume is a C4-C12 thio-damascone.
I. A product comprising the freshening composition according to any of Paragraphs A-H, wherein the product comprises a propellant.
J. The product of Paragraph I, wherein the propellant comprises compressed gas or a hydrocarbon.
K. The product according to any of Paragraphs I-J, wherein the freshening composition is contained in a transparent or translucent spray dispenser.
L. The product according to any of Paragraphs I-K, wherein the freshening composition is contained in a plastic spray dispenser.
M. The freshening composition according to any of Paragraphs A-L, wherein the freshening composition is an aqueous composition.
N. The freshening composition according to any of Paragraphs A-M, wherein the freshening composition is free of primary amines.
O. A method of freshening the air, the method comprising the step of:
   providing a freshening composition, the freshening composition comprising:
      about 0.02 wt. % to about 1.0 wt. %, based on the weight of the composition, of a sulfur-containing pro-perfume;
      about 0.2 wt. % to about 1.4 wt. %, based on the weight of the composition, of a perfume mixture, the perfume mixture comprising at least one perfume material selected from the group consisting of: 3-(1,3-Benzodioxol-5-yl)-2-methylpropanal, canthoxal, vanillin, ethyl vanillin, citral, ligustral, cinnamic aldehydes, and combinations thereof; and
      a carrier; and
   spraying the freshening composition into the air in the form of spray droplets.
P. The method of Paragraph 0, wherein the spray droplets have a mean particle size from about 10 microns to about 100 microns.
Q. The method according to any of Paragraphs O-P, wherein the freshening composition is contained in a spray dispenser, wherein the spray dispenser further comprises a compressed gas propellant.
R. The method according to any of Paragraphs O-Q, wherein the spray dispenser comprises plastic.
S. The method of Paragraph Q or R, wherein the spray dispenser is transparent or translucent.
T. The method according to any of Paragraphs O-S, wherein the freshening composition is contained in a spray dispenser, wherein the spray dispenser further comprises a hydrocarbon propellant.

U. The method according to any of Paragraphs O-T, wherein the step of spraying the freshening composition further comprises spraying the freshening composition at a flow rate in the range of about 0.1 g/s to about 2.5 g/s.
V. The method according to any of Paragraphs O-U, wherein the freshening composition further comprises a carboxylic acid, wherein the carboxylic acid is preferably citric acid or polyacrylic acid.
W. The method according to any of Paragraphs O-V, wherein the freshening composition further comprises a secondary or tertiary amine.
X. The method of Paragraph W, wherein the freshening composition comprises a weight ratio of carboxylic acid to secondary or tertiary amine of equal to or greater than 3:1.
Y. The method according to any of Paragraphs O-X, wherein the freshening composition is an aqueous composition.
Z. The method according to any of Paragraphs O-X, wherein the freshening composition is free of primary amines.
AA. The method according to any of Paragraphs O-Z, wherein the freshening composition comprises a weight ratio of perfume mixture to sulfur-containing pro-perfume of about 3:1 to about 35:1, more preferably about 8:1 to about 25:1, most preferably about 10:1 to about 20:1, by weight of the freshening composition.
BB. The method according to any of Paragraphs O-AA, wherein the sulfur-containing pro-perfume is present at a level of about 0.02 wt. % to about 1.0 wt. %, preferably about 0.02 wt. % to about 0.8 wt. %, more preferably about 0.03 wt. % to about 0.3 wt. %, most preferably about 0.03 wt % to about 0.09 wt %, by weight of the freshening composition.
CC. The method according to any of Paragraphs O-BB, wherein the sulfur-containing pro-perfume is a C4-C12 thio-damascone.
DD. The method according to any of Paragraphs O-CC, wherein the freshening composition comprises a pH in the range of about 3 to about 8.5.
EE. The method according to any of Paragraphs O-DD, wherein the freshening composition comprises a pH in the range of about 4 to about 6.5.
FF. A freshening composition comprising:
  a sulfur-containing pro-perfume;
  a perfume mixture comprising an aldehyde or ketone;
  a secondary or tertiary amine;
  a carboxylic acid buffer; and
  an aqueous carrier, wherein the composition has a weight ratio of carboxylic acid buffer to secondary or tertiary amine of equal to or greater than 3:1, based on the weight of the composition.
GG. The freshening composition of Paragraph FF, wherein the composition is free of primary amines.
HH. The freshening composition according to any of Paragraphs FF-GG, wherein the perfume mixture comprises a perfume raw material selected from the group consisting of: 3-(1,3-Benzodioxol-5-yl)-2-methylpropanal, canthoxal, vanillin, ethyl vanillin, citral, ligustral, cinnamic aldehydes, and combinations thereof.
II. The freshening composition according to any of Paragraphs FF-HH, wherein the freshening composition comprises a pH in the range of about 3 to about 8.5, more preferably about 4 to about 6.5.
JJ. The freshening composition according to any of Paragraphs FF-II, wherein the carboxylic acid buffer is citric acid or polyacrylic acid.
KK. The freshening composition according to any of Paragraphs FF-JJ, wherein the freshening composition comprises a weight ratio of perfume mixture to sulfur-containing pro-perfume of about 3:1 to about 35:1, more preferably about 8:1 to about 25:1, most preferably about 10:1 to about 20:1, by weight of the freshening composition.
LL. The freshening product according to any of Paragraphs FF-KK, wherein the sulfur-containing pro-perfume is present at a level of about 0.03 wt % to about 0.09 wt %, by weight of the freshening composition. wherein the sulfur-containing pro-perfume is present at a level of about 0.02 wt. % to about 1.0 wt. %, preferably about 0.02 wt. % to about 0.8 wt. %, more preferably about 0.03 wt. % to about 0.3 wt. %, most preferably about 0.03 wt % to about 0.09 wt %, by weight of the freshening composition.
MM. The freshening composition according to any of Paragraphs FF-LL, wherein the sulfur-containing pro-perfume is a C4-C12 thio-damascone.
NN. A product comprising the freshening composition according to any of Paragraphs FF-MM, wherein the product comprises a compressed gas or hydrocarbon propellant.
OO. The product according to any of Paragraphs NN, wherein the freshening composition is contained in a transparent or translucent spray dispenser.
PP. The product according to any of Paragraphs NN-OO, wherein the freshening composition is contained in a plastic spray dispenser.

DETAILED DESCRIPTION

Figure 1:
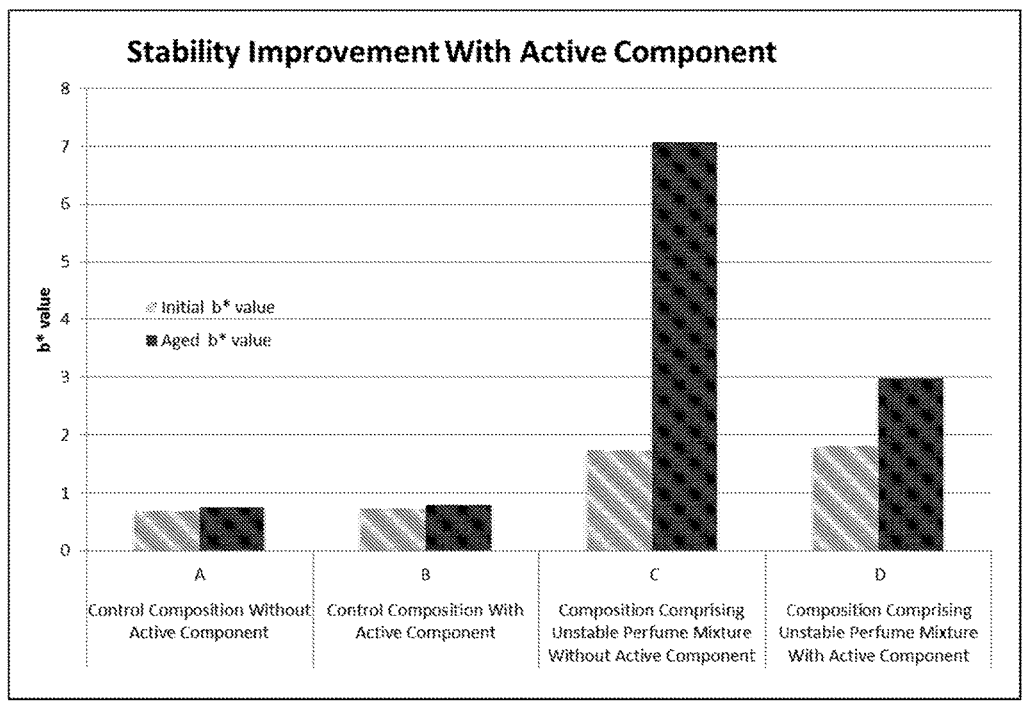
FIG. 1 is a plot of the initial and Aged b* values of Compositions A-D.

The freshening composition of the present disclosure is designed to extend scent release into the air or onto an inanimate surface. Such prolonged freshness and malodor reduction may last for at least about four hours, or at least about six hours, or at least about eight hours, or at least about 24 hours, or at least about 48 hours after treating a space with the freshening composition. The freshening compositions of the present disclosure may also deliver relatively consistent scent over an extended period of time. Moreover, the freshening compositions of the present disclosure may be designed to be stable over an extended shelf-life.

The freshening composition of the present disclosure comprises a sulfur-containing pro-perfume, perfume raw material(s), and a carrier.

Sulfur-Containing Pro-Perfume

The term "sulfur-containing pro-perfume" herein refers to a type of pro-perfume compound that contains sulfur. The term "pro-perfume" herein refers to compounds resulting from the reaction of perfume materials ("PRMs" or, singularly, "PRM") with other chemicals, which have a covalent bond between one or more PRMs and these other chemicals. The PRM is converted into a new material called a pro-perfume compound, which then may release the original PRM (i.e., pre-converted) upon exposure to a trigger such as water or light or atmospheric oxygen. Suitable pro-perfume compounds and methods of making the same can be found in U.S. Pat. Nos. 7,018,978; 6,861,402; 6,544,945; 6,093,691; 6,165,953; and 6,096,918.

The sulfur-containing pro-perfume herein may comprise a compound of formula (I):

$$Y-S-G-Q \tag{I}$$

wherein:
(i) Y is a radical selected from the group consisting of (Y-1) to (Y-7) shown herein below, including isomeric forms:

(Y-1)
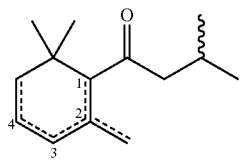

(Y-2)
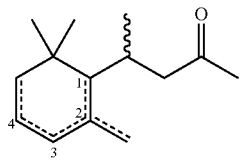

(Y-3)
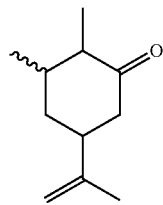

(Y-4)
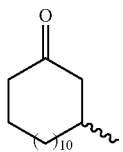

(Y-5)
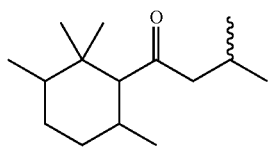

(Y-6)
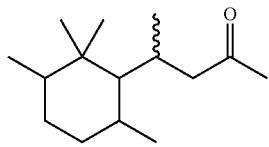

(Y-7)
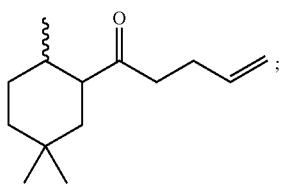

wherein the wavy lines represent the location of the sulfur (S) bond, and the dotted lines represent a single or double bond;

(ii) G is selected from a divalent or trivalent radical derived from a linear or branched alkyl or alkenyl radical having from 2 to 15 carbon atoms; and (iii) Q is selected from a hydrogen, a —S—Y group, or a —NR$^2$—Y group, wherein Y is independently selected as defined above, and R$^2$ is selected from a hydrogen or a C$_1$-C$_3$ alkyl group.

G may be a divalent or trivalent radical, preferably a divalent radical derived from a linear or branched alkyl or alkenyl radical having from 2 to 15 carbon atoms, substituted with one or more groups selected from the group consisting of —OR$^1$, —NR$^{12}$, —COOR$^1$, R$^1$ groups, and a combination thereof, wherein R$^1$ is selected from a hydrogen or a C$_1$ to C$_6$ alkyl or alkenyl group. Preferably, G is a divalent radical derived from a linear or branched alkyl or alkenyl radical having from 2 to 15 carbon atoms, substituted with at least one —COOR$^1$ group, preferably substituted with a —COOR$^1$ group, wherein R$^1$ is selected from a hydrogen or a C$_1$ to C$_6$ alkyl or alkenyl group. Even more preferably, G is a divalent radical derived from a linear alkyl radical having a —CH$_2$CH(COOR$^1$) group, wherein R$^1$ is a hydrogen or a methyl or ethyl group. G may be a divalent radical derived from a linear alkyl radical having from 8 to 15 carbon atoms which is either substituted or un-substituted.

The sulfur-containing pro-perfume may be a compound of formula (I) wherein Y is selected from Y-1, Y-2 or Y-3 groups as defined above, and G and Q are defined in any one of the above-described examples. The sulfur-containing pro-perfume may be a sulfide.

Preferably, the sulfur-containing pro-perfume is selected from the group consisting of methyl or ethyl 2-(4-oxo-4-(2,6,6-trimethylcyclohex-3-en-1-yl)butan-2-ylamino)-3-(4-oxo-4-(2,6,6-trimethylcyclohex-3-en-1-yl)butan-2-ylthio) propanate, methyl or ethyl 2-(4-oxo-4-(2,6,6-trimethylcyclohex-2-en-1-yl)butan-2-ylamino)-3-(4-oxo-4-(2,6,6-trimethylcyclohex-2-en-1-yl)butan-2-ylthio) propanate, methyl or ethyl 2-(2-oxo-4-(2,6,6-trimethylcyclohex-1-en-1-yl)butan-4-ylamino)-3-(2-oxo-4-(2,6,6-trimethylcyclohex-1-en-1-yl)butan-4-ylthio) propanate, methyl or ethyl 2-(2-oxo-4-(2,6,6-trimethylcyclohex-2-en-1-yl)butan-4-ylamino)-3-(2-oxo-4-(2,6,6-trimethylcyclohex-2-en-1-yl)butan-4-ylthio) propanate, 3-(dodecylthio)-1-(2,6,6-trimethylcyclohex-3-en-1-yl)-1-butanone, 3-(dodecylthio)-1-(2,6,6-trimethylcyclohex-2-en-1-yl)-1-butanone, 4-(dodecylthio)-4-(2,6,6-trimethylcyclohex-2-en-1-yl)-2-butanone, 4-(dodecylthio)-4-(2,6,6-trimethylcyclohex-1-en-1-yl)-2-butanone, 2-dodecylsulfanyl-5-methyl-heptan-4-one, 2-cyclohexyl-1-dodecylsulfanyl-hept-6-en-3-one, 3-(dodecylthio)-5-isopropenyl-2-methylcyclohexanone, and a combination thereof.

More preferably, the sulfur-containing pro-perfume compound is selected from the group consisting of 3-(dodecylthio)-1-(2,6,6-trimethylcyclohex-3-en-1-yl)-1-butanone, 4-(dodecylthio)-4-(2,6,6-trimethylcyclohex-2-enl-yl)-2-butanone, 4-(dodecylthio)-4-(2,6,6-trimethylcyclohex-1-en-1-yl)-2-butanone and 3-(dodecylthio)-5-isopropenyl-2-methylcyclohexanone, and a combination thereof. 3-(dodecylthio)-1-(2,6,6-trimethylcyclohex-3-en-1-yl)-1-butanone is the most preferred sulfur-containing pro-perfume compound, such as Haloscent® D available from Firmenich located in Geneva, Switzerland.

The sulfur-containing pro-perfume compound may be present at various levels in the composition. Preferably, the sulfur-containing pro-perfume compound is present in an amount from about 0.01% to about 1.0%, alternatively from about 0.02% to about 0.8%, alternatively from about 0.03% to about 0.5%, alternatively about 0.03% to about 0.3%, alternatively about 0.03% to about 0.09%, alternatively at least about 0.02%, alternatively at least about 0.03%, alternatively at least about 0.04%, alternatively at least about 0.05%, by weight of the composition.

The freshening composition may comprise dodecyl thio-damascone having the general structure shown below.

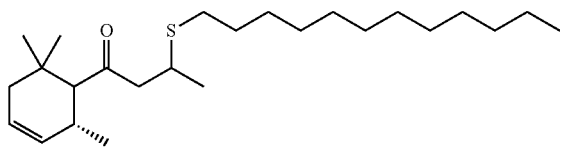 [SMILES: CCCCCCCCCCCCSC(C)CC(=O)C1[C@H](C)C=CCC1(C)C]

Thio-damascone may be present in an amount from about 0.01% to about 1.0%, alternatively from about 0.02% to about 0.8%, alternatively from about 0.03% to about 0.5%, alternatively about 0.03% to about 0.3%, alternatively about 0.03% to about 0.09%, alternatively at least about 0.02%, alternatively at least about 0.03%, alternatively at least about 0.04%, alternatively at least about 0.05%, by weight of the composition.

Perfume Mixture

The freshening composition also includes a perfume mixture comprising at least one perfume raw materials (PRMs). Various PRMs may be used. The freshening composition may include a perfume mixture comprising one or more of the following perfume raw materials. As used herein, a "perfume raw material" refers to one or more of the following ingredients: fragrant essential oils; aroma compounds; pro-perfumes; materials supplied with the fragrant essential oils, aroma compounds, and/or pro-perfumes, including stabilizers, diluents, processing agents, and contaminants; and any material that commonly accompanies fragrant essential oils, aroma compounds, and/or pro-perfumes.

The PRM may include one or more ketones. The PRM comprising ketone can comprise any PRMs which contain one or more ketone moieties and which can impart a desirable scent. The PRM may comprise ketone comprising a PRM selected from the group consisting of buccoxime; iso jasmone; methyl beta naphthyl ketone; musk indanone; tonalid/musk plus; alpha-damascone, beta-damascone, delta-damascone, iso-damascone, damascenone, damarose, methyl-dihydrojasmonate, menthone, carvone, camphor, fenchone, alpha-ionone, beta-ionone, dihydro-beta-ionone, gamma-methyl so-called ionone, fleuramone, dihydrojasmone, cis-jasmone, iso-e-super, methyl-cedrenyl-ketone or methyl-cedrylone, acetophenone, methyl-acetophenone, para-methoxy-acetophenone, methyl-beta-naphtyl-ketone, benzyl-acetone, benzophenone, para-hydroxy-phenyl-butanone, celery ketone or livescone, 6-isopropyldecahydro-2-naphtone, dimethyl-octenone, freskomenthe, 4-(1-ethoxyvinyl)-3,3,5,5,-tetramethyl-cyclohexanone, methyl-heptenone, 2-(2-(4-methyl-3-cyclohexen-1-yl)propyl)-cyclopentanone, 1-(p-menthen-6(2)-yl)-1-propanone, 4-(4-hydroxy-3-methoxyphenyl)-2-butanone, 2-acetyl-3,3-dimethyl-norbornane, 6,7-dihydro-1,1,2,3,3-pentamethyl-4 (5h)-indanone, 4-damascol, dulcinyl or cassione, gelsone, hexalon, isocyclemone e, methyl cyclocitrone, methyl-lavender-ketone, orivon, para-tertiary-butyl-cyclohexanone, verdone, delphone, muscone, neobutenone, plicatone, veloutone, 2,4,4,7-tetramethyl-oct-6-en-3-one, tetrameran, hedione, floralozone, gamma undecalactone, ethylene brassylate, pentadecanolide, methyl nonyl ketone, cyclopentadecanone, cyclic ethylene dodecanedioate, 3,4,5,6-tetrahydropseudoionone, 8-hexadecenolide, dihydrojasmone, 5-cyclohexadecenone, and a combination thereof.

The PRM comprising ketone comprises a PRM selected from the group consisting of alpha-damascone, delta-damascone, iso-damascone, carvone, gamma-methyl-ionone, beta-ionone, iso-e-super, 2,4,4,7-tetramethyl-oct-6-en-3-one, benzyl acetone, beta-damascone, damascenone, methyl dihydrojasmonate, methyl cedrylone, hedione, floralozone, and a combination thereof. Preferably, the PRM comprising ketone comprises delta-damascone.

The freshening composition may include a mixture of aldehydes that contribute to scent character and neutralize malodors in vapor and/or liquid phase via chemical reactions. Aldehydes that are partially reactive or volatile may be considered a reactive aldehyde as used herein. Reactive aldehydes may react with amine-based odors, following the path of Schiff-base formation. Reactive aldehydes may also react with sulfur-based odors, forming thiol acetals, hemi thiolacetals, and thiol esters in vapor and/or liquid phase. It may be desirable for these vapor and/or liquid phase reactive aldehydes to have virtually no negative impact on the desired perfume character, color or stability of a product.

The freshening composition may include a mixture of aldehydes that are partially volatile which may be considered a volatile aldehyde as used herein. The volatile aldehydes may also have a certain boiling point (B.P.) and octanol/water partition coefficient (P). The boiling point referred to herein is measured under normal standard pressure of 760 mmHg. The boiling points of many volatile aldehydes, at standard 760 mm Hg are given in, for example, "Perfume and Flavor Chemicals (Aroma Chemicals)," written and published by Steffen Arctander, 1969.

The octanol/water partition coefficient of a volatile aldehyde is the ratio between its equilibrium concentrations in octanol and in water. The partition coefficients of the volatile aldehydes used in the malodor control composition may be more conveniently given in the form of their logarithm to the base 10, log P. The log P values of many volatile aldehydes have been reported. See, e.g., the Pomona92 database, available from Daylight Chemical Information Systems, Inc. (Daylight CIS), Irvine, Calif. However, the log P values are most conveniently calculated by the "C LOG P" program, also available from Daylight CIS. This program also lists experimental log P values when they are available in the Pomona92 database. The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each volatile aldehyde, and takes into account the numbers and types of atoms, the atom connectivity, and chemical bonding. The C log P values, which are the most reliable and widely used estimates for this physicochemical property, are preferably used instead of the experimental log P values in the selection of volatile aldehydes for the malodor control composition.

The C log P values may be defined by four groups and the volatile aldehydes may be selected from one or more of these groups. The first group comprises volatile aldehydes that have a B.P. of about 250° C. or less and C log P of about 3 or less. The second group comprises volatile aldehydes that have a B.P. of 250° C. or less and C log P of 3.0 or more. The third group comprises volatile aldehydes that have a B.P. of 250° C. or more and C log P of 3.0 or less. The fourth group comprises volatile aldehydes that have a B.P. of 250° C. or more and C log P of 3.0 or more. The malodor control composition may comprise any combination of volatile aldehydes from one or more of the C log P groups.

The malodor control composition may comprises, by total weight of the freshening composition, from about 0% to about 30% of volatile aldehydes from group 1, alternatively about 25%; and/or about 0% to about 10% of volatile aldehydes from group 2, alternatively about 10%; and/or from about 10% to about 30% of volatile aldehydes from group 3, alternatively about 30%; and/or from about 35% to about 60% of volatile aldehydes from group 4, alternatively about 35%.

Exemplary reactive and/or volatile aldehydes which may be used in a freshening composition include, but are not limited to, Adoxal (2,6,10-Trimethyl-9-undecenal), Bourgeonal (4-t-butylbenzenepropionaldehyde), Lilestralis 33 (2-methyl-4-t-butylphenyl)propanal), Cinnamic aldehyde, cinnamaldehyde (phenyl propenal, 3-phenyl-2-propenal), Citral, Geranial, Neral (dimethyloctadienal, 3,7-dimethyl-2,6-octadien-1-al), Cyclal C (2,4-dimethyl-3-cyclohexen-1-carbaldehyde), Florhydral (3-(3-Isopropyl-phenyl)-butyraldehyde), Citronellal (3,7-dimethyl 6-octenal), Cymal, cyclamen aldehyde, Cyclosal, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), Helional (3-(1,3-Benzodioxol-5-yl)-2-methylpropanal; 2-Methyl-3-(3,4-methylenedioxyphenyl) propanal), Intreleven aldehyde (undec-10-en-1-al), Ligustral, Trivertal (2,4-dimethyl-3-cyclohexene-1-carboxaldehyde), Jasmorange, satinaldehyde (2-methyl-3-tolyl-proionaldehyde, 4-dimethylbenzenepropanal), Lyral (4-(4-hydroxy-4-methyl pentyl)-3-cyclohexene-1-carboxaldehyde), Melonal (2,6-Dimethyl-5-Heptenal), Methoxy Melonal (6-methoxy-2,6-dimethylheptanal), methoxycinnamaldehyde (trans-4-methoxycinnamaldehyde), Myrac aldehyde isohexenyl cyclohexenyl-carboxaldehyde, trifernal ((3-methyl-4-phenyl propanal, 3-phenyl butanal), lilial, P.T. Bucinal, lysmeral, benzenepropanal (4-tert-butyl-alpha-methyl-hydrocinnamaldehyde), Dupical, tricyclodecylidenebutanal (4-Tricyclo5210-2,6decylidene-8butanal), Melafleur (1,2,3,4,5,6,7,8-octahydro-8,8-dimethyl-2-naphthaldehyde), Methyl Octyl Acetaldehyde, aldehyde C-11 MOA (2-mehtyl deca-1-al), Onicidal (2,6,10-trimethyl-5,9-undecadien-1-al), Citronellyl oxyacetaldehyde, Muguet aldehyde 50 (3,7-dimethyl-6-octenyl) oxyacetaldehyde), phenylacetaldehyde, Mefranal (3-methyl-5-phenyl pentanal), Triplal, Vertocitral dimethyl tetrahydrobenzene aldehyde (2,4-dimethyl-3-cyclohexene-1-carboxaldehyde), 2-phenylproprionaldehyde, Hydrotropaldehyde, Canthoxal, anisylpropanal 4-methoxy-alpha-methyl benzenepropanal (2-anisylidene propanal), Cylcemone A (1,2,3,4,5,6,7,8-octahydro-8,8-dimethyl-2-naphthaldehyde), and Precylcemone B (1-cyclohexene-1-carboxaldehyde).

Still other exemplary aldehydes include, but are not limited to, acetaldehyde (ethanal), pentanal, valeraldehyde, amylaldehyde, Scentenal (octahydro-5-methoxy-4,7-Methano-1H-indene-2-carboxaldehyde), propionaldehyde (propanal), Cyclocitral, beta-cyclocitral, (2,6,6-trimethyl-1-cyclohexene-1-acetaldehyde), Iso Cyclocitral (2,4,6-trimethyl-3-cyclohexene-1-carboxaldehyde), isobutyraldehyde, butyraldehyde, isovaleraldehyde (3-methyl butyraldehyde), methylbutyraldehyde (2-methyl butyraldehyde, 2-methyl butanal), Dihydrocitronellal (3,7-dimethyl octan-1-al), 2-Ethylbutyraldehyde, 3-Methyl-2-butenal, 2-Methylpentanal, 2-Methyl Valeraldehyde, Hexenal (2-hexenal, trans-2-hexenal), Heptanal, Octanal, Nonanal, Decanal, Lauric aldehyde, Tridecanal, 2-Dodecanal, Methylthiobutanal, Glutaraldehyde, Pentanedial, Glutaric aldehyde, Heptenal, cis or trans-Heptenal, Undecenal (2-, 10-), 2,4-octadienal, Nonenal (2-, 6-), Decenal (2-, 4-), 2,4-hexadienal, 2,4-Decadienal, 2,6-Nonadienal, Octenal, 2,6-dimethyl 5-heptenal, 2-isopropyl-5-methyl-2-hexenal, Trifernal, beta methyl Benzenepropanal, 2,6,6-Trimethyl-1-cyclohexene-1-acetaldehyde, phenyl Butenal (2-phenyl 2-butenal), 2.Methyl-3(p-isopropylphenyl)-propionaldehyde, 3-(p-isopropylphenyl)-propionaldehyde, p-Tolylacetaldehyde (4-methylphenylacetaldehyde), Anisaldehyde (p-methoxybenzene aldehyde), Benzaldehyde, Vernaldehyde (1-Methyl-4-(4-methylpentyl)-3-cyclohexenecarbaldehyde), Heliotropin (piperonal) 3,4-Methylene dioxy benzaldehyde, alpha-Amylcinnamic aldehyde, 2-pentyl-3-phenyl-propenoic aldehyde, Vanillin (4-methoxy 3-hydroxy benzaldehyde), Ethyl vanillin (3-ethoxy 4-hydroxybenzaldehyde), Hexyl Cinnamic aldehyde, Jasmonal H (alpha-n-hexylcinnamaldehyde), Floralozone, (para-ethyl-alpha,alpha-dimethyl Hydrocinnamaldehyde), Acalea (p-methyl-alpha-pentylcinnamaldehyde), methylcinnamaldehyde, alpha-Methylcinnamaldehyde (2-methyl 3-pheny propenal), alpha-hexylcinnamaldehyde (2-hexyl 3-phenyl propenal), Salicylaldehyde (2-hydroxy benzaldehyde), 4-ethyl benzaldehyde, Cuminaldehyde (4-isopropyl benzaldehyde), Ethoxybenzaldehyde, 2,4-dimethylbenzaldehyde, Veratraldehyde (3,4-dimethoxybenzaldehyde), Syringaldehyde (3,5-dimethoxy 4-hydroxybenzaldehyde), Catechaldehyde (3,4-dihydroxybenzaldehyde), Safranal (2,6,6-trimethyl-1,3-diene methanal), Myrtenal (pin-2-ene-1-carbaldehyde), Perillaldehyde L-4(1-methylethenyl)-1-cyclohexene-1-carboxaldehyde), 2,4-Dimethyl-3-cyclohexene carboxaldehyde, 2-Methyl-2-pentenal, 2-methylpentenal, pyruvaldehyde, formyl Tricyclodecan, Mandarin aldehyde, Cyclemax, Pino acetaldehyde, Corps Iris, Maceal, and Corps 4322.

The perfume mixture may include a perfume mixture of one or more perfume raw materials from Table 1.

TABLE 1

Perfume Raw Materials

| CAS # | Name |
|---|---|
| 31375-17-4 | 1-(p-menthen-6(2)-yl)-1-propanone |
| 95962-14-4 | 2-(2-(4-methyl-3-cyclohexen-1-yl)propyl)-cyclopentanone |
| 74338-72-0 | 2,4,4,7-tetramethyl-oct-6-en-3-one |
| 42370-07-0 | 2-acetyl-3,3-dimethyl-norbornane |
| 4433-36-7 | 3,4,5,6-tetrahydropseudoionone |
| 36306-87-3 | 4-(1-ethoxyvinyl)-3,3,5,5,-tetramethyl-cyclohexanone |
| 122-48-5 | 4-(4-hydroxy-3-methoxyphenyl)-2-butanone |
| 4927-36-0 | 4-damascol |
| 37609-25-9 | 5-cyclohexadecenone |
|  | 6-isopropyldecahydro-2-naphtone |
|  | 8-hexadecenolide |
| 127-41-3 | alpha-ionone |
| 127-42-4 | alpha-Methyl Ionone |
| 119-61-9 | Benzophenone |
| 2550-26-7 | benzyl-acetone |
| 75147-23-8 | Buccoxime |
|  | Cassione |
| 3720-16-9 | celery ketone |
| 91462-24-7 | cyclic ethylene dodecanedioate |
| 502-72-7 | Cyclopentadecanone |
| 43052-87-5 | damarose alpha |
| 23696-85-7 | Damascenone |
| 2550-11-0 | dimethyl-octenone |
| 55418-52-5 | Dulcinyl |
| 105-95-3 | ethylene brassylate |
| 67634-14-4 | Floralozone |
| 706-14-9 | Gamma Decalactone |
| 127-51-5 | gamma-methyl ionone |
| 104-50-7 | gamma-Octalactone |
| 108-29-2 | gamma-Valero Lactone |
| 29214-60-6 | Gelsone |
| 24851-98-7 | Hedione |
| 79-78-7 | Hexalon |

TABLE 1-continued

Perfume Raw Materials

| CAS # | Name |
|---|---|
| 54464-57-2 | isocyclemone e |
| 70266-48-7 | iso-damascone |
| 54464-57-2 | iso-e-super |
| 24851-98-7 | methy-dihydrojasmonate |
|  | methyl beta naphthyl ketone |
| 32388-55-9 | Methyl Cedrylone Major |
| 122-00-9 | methyl-acetophenone |
|  | methyl-beta-naphtyl-ketone |
| 32388-55-9 | methyl-cedrenyl-ketone |
| 32388-55-9 | methyl-cedrylone |
| 110-93-0 | methyl-heptenone |
| 67633-95-8 | methyl-lavender-ketone |
| 541-91-3 | Muscone |
| 127-43-5 | n-beta-Methyl Ionone Isomer |
| 56973-85-4 | Neobutenone |
| 16587-71-6 | Orivone |
| 5471-51-2 | Para Hydroxy Phenyl Butanone |
| 100-06-1 | para-methoxy-acetophenone |
| 98-53-3 | para-tert-butyl-cyclohexanone |
| 106-02-5 | pentadecanolide |
| 5471-51-2 | p-Hydroxy Phenyl Butanone |
| 1322-58-3 | Tetrameran |
| 21145-77-7 | Tonalid |
| 68991-97-9 | 1,2,3,4,5,6,7,8-octahydro-8,8-dimethyl-2-naphthaldehyde |
| 1192-88-7 | 1-cyclohexene-1-carboxaldehyde |
| 66327-54-6 | 1-Methyl-4-(4-methylpentyl)-3-cyclohexenecarbaldehyde |
| 1335-66-6 | 2,4,6-trimethyl-3-cyclohexene-1-carboxaldehyde |
| 25152-84-5 | 2,4-Decadienal |
| 68039-49-6 | 2,4-dimethyl-3-cyclohexen-1-carbaldehyde |
| 68039-49-6 | 2,4-Dimethyl-3-cyclohexene carboxaldehyde |
| 68039-49-6 | 2,4-dimethyl-3-cyclohexene-1-carboxaldehyde |
| 15764-16-6 | 2,4-dimethylbenzaldehyde |
| 68737-61-1 | 2,4-Dimethylcyclohex-3-ene-1-carbaldehyde |
| 142-83-6 | 2,4-hexadienal |
| 30361-28-5 | 2,4-octadienal |
| 24048-13-3 | 2,6,10-trimethyl-5,9-undecadien-1-al |
| 141-13-9 | 2,6,10-Trimethyl-9-undecenal |
| 116-26-7 | 2,6,6-trimethyl-1,3-diene methanal |
| 472-66-2 | 2,6,6-Trimethyl-1-cyclohexene-1-acetaldehyde |
| 106-72-9 | 2,6-dimethyl 5-heptenal |
| 26370-28-5 | 2,6-Nonadienal |
| 103-95-7 | 2.Methyl-3-(p-isopropylphenyl)-propionaldehyde |
| 112-54-9 | 2-Dodecanal |
| 613-69-4 | 2-Ethoxybenzaldehyde |
| 97-96-1 | 2-Ethylbutyraldehyde |
| 6728-26-3 | 2-hexenal |
| 101-86-0 | 2-hexyl 3-phenyl propenal |
| 90-02-8 | 2-hydroxy benzaldehyde |
| 35158-25-9 | 2-isopropyl-5-methyl-2-hexenal |
| 101-39-3 | 2-methyl 3-phenyl propenal |
| 96-17-3 | 2-methyl butyraldehyde |
|  | 2-methyl deca-1-al |
| 123-15-9 | 2-Methyl Valeraldehyde |
| 110-41-8 | 2-methyl-1-undecanal |
| 623-36-9 | 2-Methyl-2-pentenal |
| 1205-17-0 | 2-Methyl-3-(3,4-methylenedioxyphenyl)propanal |
|  | 2-methyl-3-tolylproionaldehyde, 4-dimethylbenzene-propanal |
| 80-54-6 | 2-methyl-4-t-butylphenyl)propanal |
| 123-15-9 | 2-Methylpentanal |
| 623-36-9 | 2-methylpentenal |
| 122-40-7 | 2-pentyl-3-phenylpropenoic aldehyde |
| 4411-89-6 | 2-phenyl 2-butenal |
| 93-53-8 | 2-phenylproprionaldehyde |
| 125109-85-5 | 3-(3-Isopropyl-phenyl)-butyraldehyde |
| 103-95-7 | 3-(p-isopropylphenyl)-propionaldehyde |
| 139-85-5 | 3,4-dihydroxybenzaldehyde |
| 120-14-9 | 3,4-dimethoxybenzaldehyde |
| 120-57-0 | 3,4-Methylene dioxy benzaldehyde |
| 134-96-3 | 3,5-dimethoxy 4-hydroxybenzaldehyde |
| 106-23-0 | 3,7-dimethyl 6-octenal |
| 107-75-5 | 3,7-dimethyl octan-1-al |
| 106-24-1 | 3,7-dimethyl-2,6-octadien-1-al |
| 7492-67-3 | 3,7-dimethyl-6-octenyl oxyacetaldehyde |
| 121-32-4 | 3-ethoxy 4-hydroxybenzaldehyde |
| 590-86-3 | 3-methyl butyraldehyde |
| 107-86-8 | 3-Methyl-2-butenal |
| 55066-49-4 | 3-methyl-5-phenyl pentanal |
| 16251-77-7 | 3-phenyl butanal |
| 31906-04-4 | 4-(4-hydroxy-4-methyl pentyl)-3-cyclohexene-1-carboxaldehyde |
| 10031-82-0 | 4-Ethoxybenzaldehyde |
| 4748-78-1 | 4-ethyl benzaldehyde |
| 122-03-2 | 4-isopropyl benzaldehyde |
| 621-59-0 | 4-methoxy 3-hydroxy benzaldehyde |
| 5703-26-4 | 4-methylphenylacetaldehyde |
| 18127-01-0 | 4-t-butylbenzenepropionaldehyde |
| 80-54-6 | 4-tert-butyl-alpha-methyl-hydrocinnamaldehyde |
|  | 4-Tricyclo5210-2,6decylidene-8butanal |
| 62439-41-2 | 6-methoxy-2,6-dimethylheptanal |
| 107-75-5 | 7-hydroxy-3,7-dimethyl octan-1-al |
| 84697-09-6 | Acalea |
| 75-07-0 | Acetaldehyde |
| 141-13-9 | Adoxal |
| 19009-56-4 | aldehyde C-11 MOA |
| 110-41-8 | aldehyde C12 MNA |
| 122-40-7 | alpha-Amylcinnamic aldehyde |
| 101-86-0 | alpha-hexylcinnamaldehyde |
| 101-39-3 | alpha-Methylcinnamaldehyde |
| 103-95-7 | Alpha-methyl-p-isopropyl phenyl propyl aldehyde |
| 101-86-0 | alpha-n-hexyl-cinnamaldehyde |
| 122-40-7 | Amyl Cinnamic Aldehyde |
| 495-85-2 | Amylaldehyde |
| 123-11-5 | Anisic aldehyde |
| 5462-06-6 | Anisylpropanal |
| 100-52-7 | Benzaldehyde |
| 104-53-0 | benzenepropanal |
| 65885-41-8 | beta methyl Benzenepropanal |
| 432-25-7 | beta-cyclocitral |
| 18127-01-0 | Bourgeonal |
| 123-72-8 | Butyraldehyde |
| 5462-06-6 | Canthoxal |
| 139-85-5 | Catechaldehyde |
| 104-55-2 | Cinnamic Aldehyde |
| 6728-31-0 | cis-Heptenal |
| 5392-40-5 | Citral |
| 106-23-0 | Citronellal |
| 107-75-5 | citronellal hydrate |
| 7492-67-3 | citronellyl oxyacetaldehyde |
|  | Corps 4322 |
|  | Corps Iris |
| 122-03-2 | Cuminaldehyde |
| 68039-49-6 | cyclal C |
| 103-95-7 | cyclamen aldehyde |
| 7775-00-0 | Cyclemax |
| 68738-96-5 | cyclemone A |
|  | Cyclocitral |
| 31906-04-4 | cyclohexenyl-carboxaldehyde |
| 103-95-7 | Cymal |
| 112-31-2 | Decenal |
| 5988-91-0 | Dihydrocitronellal |
| 30168-23-1 | Duplical |
| 75-07-0 | ethanal |
| 121-32-4 | Ethyl Vanillin |
| 97-53-0 | Eugenol |
| 71077-31-1 | Floral super |
| 67634-14-4 | Floralozone |
| 125109-85-5 | Florhydral |
|  | formyl Tricyclodecan |
| 5392-40-5 | Geranial |
| 111-30-8 | Glutaraldehyde |
| 111-30-8 | Glutaric aldehyde |
| 1205-17-0 | Helional (3-(1,3-Benzodioxol-5-yl)-2-methylpropanal) |
| 120-57-0 | Heliotropin |
| 111-71-7 | Heptanal |
| 66-25-1 | Hexenal |
| 101-86-0 | Hexyl Cinnamic aldehyde |
| 90-87-9 | Hydrotropaldehyde |
| 107-75-5 | hydroxycitronellal |
| 1337-83-3 | Intreleven aldehyde |
| 1335-66-6 | Iso Cyclocitral |
| 78-84-2 | isobutyraldehyde |

TABLE 1-continued

Perfume Raw Materials

| CAS # | Name |
|---|---|
| 1335-66-6 | iso-Cyclo Citral |
| 590-86-3 | isovaleraldehyde |
| 101-86-0 | Jasmonal H |
| 41496-43-9 | Jasmorange |
| 2111-75-3 | L-4(1-methylethenyl)-1-cyclohexene-1-carboxaldehyde |
| 112-54-9 | lauric aldehyde |
| 68039-49-6 | Ligustral |
| 62518-65-4 | Lilestralis 33 |
| 80-54-6 | Lilial |
|  | lime aldehyde |
| 51414-25-6 | Lyral |
| 80-54-6 | Lysmeral |
| 67845-30-1 | Maceal |
| 20407-84-5 | Mandarinal |
| 62518-65-4 | Mefloral |
| 55066-49-4 | Mefranal |
| 68991-97-9 | Melafleur |
| 106-72-9 | Melonal |
| 62439-41-2 | methoxy melonal |
|  | methoxycinnamaldehyde |
| 93-16-3 | Methyl isoeugenol |
| 110-41-8 | methyl nonyl acetaldehyde |
| 19009-56-4 | methyl octyl acetylaldehyde |
| 96-17-3 | methylbutyraldehyde |
| 101-39-3 | methylcinnamaldehyde |
|  | Methylthiobutanal |
| 7492-67-3 | muget aldehyde 50 |
| 37677-14-8 | myrac aldehyde |
| 564-94-3 | Myrtenal |
| 173445-65-3 | Neo hivernal |
| 106-26-3 | Neral |
| 124-19-6 | Nonanal |
| 18829-56-6 | Nonenal |
| 86803-90-9 | octahydro-5-methoxy-4,7-Methano-1H-indene-2-carboxaldehyde |
| 124-13-0 | Octanal |
| 2548-87-0 | Octenal |
|  | Onicidal |
| 80-54-6 | P.T. Bucinal |
| 67634-14-4 | para-ethyl-alpha,alpha-dimethyl Hydrocinnamaldehyde |
| 110-62-3 | Pentanal |
| 111-30-8 | Pentanedial |
| 2111-75-3 | Perillaldehyde |
| 4411-89-6 | phenyl Butenal |
| 14371-10-9 | phenyl propenal, 3-phenyl-2-propenal |
| 122-78-1 | phenylacetaldehyde |
| 564-94-3 | pin-2-ene-1-carbaldehyde |
| 33885-51-7 | Pino acetaldehyde |
| 123-11-5 | p-methoxybenzene aldehyde |
| 101-39-3 | p-methyl-alpha-pentylcinnamaldehyde |
| 52474-60-9 | Precyclemeone B |
| 123-38-6 | Propanal |
| 123-38-6 | propionaldehyde |
| 104-09-6 | p-Tolylacetaldehyde |
| 78-98-8 | Pyruvaldehyde |
| 116-26-7 | Safranal |
| 90-02-8 | Salicylaldehyde |
| 41496-43-9 | Satinaldehyde |
| 86803-90-9 | Scentenal |
| 104-09-6 | Syringaldehyde |
| 21944-98-9 | Tangerinal |
| 24680-50-0 | trans-4-methoxycinnamaldehyde |
| 18829-55-5 | trans-Heptenal |
| 30168-23-1 | Tricyclodecylidenebutanal |
| 10486-19-8 | Tridecanal |
| 16251-77-7 | Trifernal |
| 68039-49-6 | Triplal |
| 67801-65-4 | Triplal extra |
| 27939-60-2 | Trivertal |
|  | undec-10-en-1-al |
| 112-44-7 | Undecenal |
| 110-62-3 | Valeraldehyde |
| 121-33-5 | Vanillin |
| 20665-85-4 | Vanillin isobutyrate |
| 120-14-9 | Veratraldehyde |
| 66327-54-6 | Vernaldehyde |
| 68039-49-6 | Vertocitral |
| 472-66-2 | β-Homocyclocitral |

The perfume mixture may include perfume raw materials selected from the group consisting of: 3-(1,3-Benzodioxol-5-yl)-2-methylpropanal (trade name Helional), canthoxal, ionone beta, indole, vanillin, ethyl vanillin, cinnamic aldehyde, maceal, triplal extra, 2,6-nonadien-1-al, ligustral, citronellal, eugenol, methyl anthranilate, dimethyl anthranilate and combinations thereof. The perfume mixture may include perfume raw materials selected from the group consisting of: 3-(1,3-Benzodioxol-5-yl)-2-methylpropanal, canthoxal, vanillin, ethyl vanillin, citral, ligustral, cinnamic aldehyde, and combinations thereof. The freshening composition may include from about 0.0001 wt % to about 5 wt %, alternatively from about 0.01 wt % to about 2 wt %, alternatively from about 0.1 wt % to 1.5 wt %, alternatively from about 0.2 wt % to about 1.4 wt %, of perfume raw materials selected from the group consisting of: 3-(1,3-Benzodioxol-5-yl)-2-methylpropanal, canthoxal, vanillin, ethyl vanillin, citral, ligustral, cinnamic aldehyde, and combinations thereof, by weight of the overall composition. The freshening composition may include from about 0.001 wt. % to about 0.5 wt. % of perfume raw materials selected from the group consisting of: 3-(1,3-Benzodioxol-5-yl)-2-methylpropanal, canthoxal, vanillin, ethyl vanillin, citral, ligustral, cinnamic aldehyde, and combinations thereof, by weight of the overall composition. The perfume mixture may comprise dimethyl anthranilate.

Such PRMs are often avoided or used at reduced concentrations because many of these PRM are unstable over time. However, it has been found that when such PRMs are combined with the sulfur-containing pro-perfume and stabilization system of the present disclosure, the stability of the composition over time is increased. Without being bound by theory, it is believed that the sulfur containing pro-perfume and stabilization system dominates over the competing reactions with the PRMs in the freshening composition via inhibiting reactions such as oxidation or other Schiff-based reactions that may lead to instability and color change and also cause undesired character shifts, off odors, reduced reactivity, poor aesthetics and or staining The cinnamic aldehydes may include cinnamic aldehyde and cinnamic aldehyde derivatives. An exemplary cinnamic aldehyde derivative may be alpha-methylcinnamaldehyde.

The total perfume mixture may be present at an amount from about 0.0001 wt % to about 10 wt %, alternatively from about 0.01 wt % to about 5 wt %, alternatively from about 0.01 wt % to about 2 wt %, alternatively from about 0.1 wt % to 1.5 wt %, alternatively from about 0.2 wt % to about 1.4 wt %, by weight of the overall composition.

The weight ratio of perfume mixture to sulfur-containing pro-perfume may be about 6:1 to about 50:1, or about 6:1 to about 35:1, or about 8:1 to about 25:1, or about 10:1 to about 20:1, by weight of the composition.

The weight ratio of perfume mixture to thio-damascone may be about 6:1 to about 50:1, or about 6:1 to about 35:1, or about 8:1 to about 25:1, or about 10:1 to about 20:1, by weight of the composition.

Without being bound by theory, it is believed that the ratio of perfume mixture to sulfur containing pro-perfume provides a minimum threshold for noticeability of freshness in the air.

Polyols

The freshening composition may comprise polyols. Low molecular weight polyols with relatively high boiling points, as compared to water, such as ethylene glycol, diethylene glycol, triethylene glycol, propylene glycol, dipropylene glycol, and/or glycerine may be utilized as a malodor counteractant for improving odor neutralization of the freshening composition. Some polyols, e.g., dipropylene glycol, are also useful to facilitate the solubilization of some perfume ingredients in the composition.

The glycol used in the freshening composition may be glycerine, ethylene glycol, propylene glycol, dipropylene glycol, polyethylene glycol, propylene glycol methyl ether, propylene glycol phenyl ether, propylene glycol methyl ether acetate, dipropylene glycol methyl ether acetate, propylene glycol n-butyl ether, dipropylene glycol n-butyl ether, dipropylene glycol n-propyl ether, ethylene glycole phenyl ether, diethylene glycol n-butyl ether, dipropylene glycol n-butyl ether, diethylene glycol mono butyl ether, dipropylene glycol methyl ether, tripropylene glycol methyl ether, tripropylene glycol n-butyl ether, other glycol ethers, or mixtures thereof. The glycol used may be ethylene glycol, propylene glycol, or mixtures thereof. The glycol used may be diethylene glycol.

Typically, the low molecular weight polyol is added to the composition at a level of from about 0.01% to about 5%, by weight of the composition, alternatively from about 0.05% to about 1%, alternatively from about 0.1% to about 0.5%, by weight of the composition. Compositions with higher concentrations may make fabrics susceptible to soiling and/or leave unacceptable visible stains on fabrics as the solution evaporates off of the fabric. The weight ratio of low molecular weight polyol to the malodor binding polymer is from about 500:1 to about 4:1, alternatively from about 1:100 to about 25:1, alternatively from about 1:50 to about 4:1, alternatively about 4:1.

Cyclodextrin

The freshening composition may include solubilized, water-soluble, uncomplexed cyclodextrin. As used herein, the term "cyclodextrin" includes any of the known cyclodextrins such as unsubstituted cyclodextrins containing from six to twelve glucose units, especially alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Cyclodextrin molecules are described in U.S. Pat. No. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the freshening composition. Freshening compositions with higher concentrations can make fabrics susceptible to soiling and/or leave unacceptable visible stains on fabrics as the solution evaporates off of the fabric. The latter is especially a problem on thin, colored, synthetic fabrics. In order to avoid or minimize the occurrence of fabric staining, the fabric may be treated at a level of less than about 5 mg of cyclodextrin per mg of fabric, alternatively less than about 2 mg of cyclodextrin per mg of fabric.

Buffer System

The freshening composition may include a buffering agent. The buffering agent may be an acidic buffering agent. The buffering agent may be a dibasic acid, carboxylic acid, or a dicarboxylic acid. The carboxylic acid may be, for example, citric acid, polyacrylic acid, or maleic acid. The acid may be sterically stable. The acid may be used in the composition for maintaining the desired pH. The freshening composition may have a pH from about 4 to about 9, alternatively from about 4 to about 8.5, alternatively from about 4 to about 6.9, alternatively about 4 to about 6.5.

Preferably, the buffer system comprises one or more buffering agents selected from the group consisting of: citric acid, maleic acid, polyacrylic acid, and combinations thereof. It has been found that buffer systems that include a buffering agent selected from the group consisting of: citric acid, maleic acid, polyacrylic acid, and combinations thereof provide stable freshening compositions with prolonged shelf life.

Preferably, the buffer system comprises citric acid and sodium citrate. It has been found that buffer systems comprising citric acid and sodium citrate provide stable freshening compositions with a prolonged shelf life.

Other suitable buffering agents for the freshening compositions include biological buffering agents. Some examples are nitrogen-containing materials, sulfonic acid buffers like 3-(N-morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine or methyldiethanolamine or derivatives thereof. Other nitrogen-containing buffering agents are tri(hydroxymethyl)amino methane (HOCH2) 3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis (methylamine)-cyclohexane, 1,3-diamino-propanol N,N'-tetra-methyl-1,3-diamino-2-propanol, N,N-bis(2-hydroxyethyl)glycine (bicine) and N-tris (hydroxymethyl)methyl glycine (tricine). Mixtures of any of the above are also acceptable.

Preferably, freshening compositions include a secondary or tertiary amine. If a secondary or tertiary amine is present, the freshening composition may have a weight ratio of sulfur-containing pro-perfume to secondary or tertiary amine of about 1:1, alternatively the weight of pro-perfume should be equal or higher than the weight of the amine, based on the total weight of the composition. If a secondary or tertiary amine is present, the weight ratio of acidic buffering agent to secondary or tertiary amine may be equal to or greater than 3:1, or greater than 5:1, or greater than 6:1.

The freshening composition may be free of primary amines. Without being bound to theory, it is believed that primary amines inhibit the sulfur-containing pro-perfume reaction with the unstable perfume raw materials.

The freshening compositions may contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

Solubilizer

The freshening composition may contain a solubilizing aid to solubilize any excess hydrophobic organic materials, particularly any PRMs, and also optional ingredients (e.g., insect repelling agent, antioxidant, etc.) which can be added to the composition, that are not readily soluble in the composition, to form a clear solution. A suitable solubilizing aid is a surfactant, such as a no-foaming or low-foaming surfactant. Suitable surfactants are anionic surfactants, nonionic surfactants, cationic surfactants, amphoteric surfactants, zwitterionic surfactants, and mixtures thereof.

The freshening composition may contain nonionic surfactants, cationic surfactants, and mixtures thereof. The freshening composition may contain surfactant derivatives of hydrogenated castor oil. Suitable ethoxylated hydrogenated castor oils that may be used in the present composition include BASOPHOR™, available from BASF, and CREMOPHOR™, available from Sigma Aldrich.

When the solubilizing agent is present, it is typically present at a level of from about 0.01% to about 3%, alternatively from about 0.05% to about 1%, alternatively from about 0.01% to about 0.05%, by weight of the freshening composition. The freshening composition may have at least as much solubilizer as sulfur-containing pro-perfume to solubilize the pro-perfume into the freshening composition. As such, the freshening composition may comprise a weight ratio of solubilizer to sulfur-containing pro-perfume in the range of about 1:1 or at least the same weight percentage of solubilizer as sulfur-containing pro-perfume, by weight of the composition.

Antimicrobial Compounds

The freshening composition may include an effective amount of a compound for reducing microbes in the air or on inanimate surfaces. Antimicrobial compounds are effective on gram negative and gram positive bacteria and fungi typically found on indoor surfaces that have contacted human skin or pets such as couches, pillows, pet bedding, and carpets. Such microbial species include *Klebsiella pneumoniae, Staphylococcus aureus, Aspergillus niger, Klebsiella pneumoniae, Steptococcus pyogenes, Salmonella choleraesuis, Escherichia coli, Trichophyton mentagrophytes*, and *Pseudomonoas aeruginosa*. The antimicrobial compounds may also effective on viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the freshening composition can be any organic material which will not cause damage to fabric appearance (e.g., discoloration, coloration such as yellowing, bleaching). Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

A quaternary compound may be used. Examples of commercially available quaternary compounds suitable for use in the freshening composition is BARQUAT® available from Lonza Corporation; and didecyl dimethyl ammonium chloride quat under the trade name BARDAC® 2250 from Lonza Corporation.

The antimicrobial compound may be present in an amount from about 500 ppm to about 7000 ppm, alternatively from about 1000 ppm to about 5000 ppm, alternatively from about 1000 ppm to about 3000 ppm, alternatively from about 1400 ppm to about 2500 ppm, by weight of the freshening composition.

Preservatives

The freshening composition may include a preservative. The preservative may be included in an amount sufficient to prevent spoilage or prevent growth of inadvertently added microorganisms for a specific period of time, but not sufficient enough to contribute to the odor neutralizing performance of the freshening composition. In other words, the preservative is not being used as the antimicrobial compound to kill microorganisms on the surface onto which the composition is deposited in order to eliminate odors produced by microorganisms. Instead, it is being used to prevent spoilage of the freshening composition in order to increase the shelf-life of the composition.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diaol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% freshening solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis {N'-[1-(hydroxymethyl)-2,5-dioxo-4-imidazolidinyl]urea}, commonly known as imidazolidinyl urea, available, e.g., under the trade name Abiol® from 3V-Sigma; Unicide U-13® from Induchem; Germall 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative are from about 0.0001% to about 0.5%, alternatively from about 0.0002% to about 0.2%, alternatively from about 0.0003% to about 0.1%, by weight of the freshening composition.

Wetting Agent

The freshening composition may, optionally, include a wetting agent that provides a low surface tension that permits the composition to spread readily and more uniformly on hydrophobic surfaces like polyester and nylon. It has been found that the freshening composition, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives and perfumes in the concentrated freshening compositions.

Non-limiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Non-limiting examples of cyclodextrin-compatible wetting agents of this type are described in U.S. Pat. No. 5,714,137 and include the Silwet® surfactants available from Momentive Performance Chemical, Albany, N.Y. Exemplary Silwet surfactants are as follows:

| Name | Average MW |
|---|---|
| L-7608 | 600 |
| L-7607 | 1,000 |
| L-77 | 600 |
| L-7605 | 6,000 |
| L-7604 | 4,000 |
| L-7600 | 4,000 |
| L-7657 | 5,000 |
| L-7602 | 3,000; | and mixtures thereof.

The total amount of surfactants (e.g. solubilizer, wetting agent) in the freshening composition is from 0% to about 3% or no more than 3%, alternatively from 0% to about 1% or no more than 1%, alternatively from 0% to about 0.9% or no more than 0.9%, alternatively from 0% to about 0.7 or no more than 0.7%, alternatively from 0% to about 0.5% or no more than 0.5%, alternatively from 0% to 0.3% or no more than about 0.3%, by weight of the composition. Compositions with higher concentrations can make fabrics susceptible to soiling and/or leave unacceptable visible stains on fabrics as the solution evaporates.

The weight ratio of sulfur-containing pro-perfume to total surfactant may be from about 1:1 to about 1:60, or from about 1:1 to about 1:30.

Carrier

The aqueous composition includes a carrier. The carrier which is used may be water. The water may be distilled, deionized, tap, or further purified forms of water. Water may be present in any amount for the composition to be an aqueous solution. Water may be present in an amount from about 85% to 99.5%, alternatively from about 90% to about 99.5%, alternatively from about 92% to about 99.5%, alternatively from about 95%, by weight of said freshening composition. Water containing a small amount of low molecular weight monohydric alcohols (e.g., ethanol, methanol, and isopropanol, or polyols, such as ethylene glycol and propylene glycol) can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the composition due to the addition of these alcohols to such things as perfumes and as stabilizers for some preservatives, the level of monohydric alcohol may be less than about 6%, alternatively less than about 3%, alternatively less than about 1%, by weight of the freshening composition.

Adjuvants can be optionally added to the freshening composition herein for their known purposes. Such adjuvants include, but are not limited to, water soluble metallic salts, antistatic agents, insect and moth repelling agents, colorants, antioxidants, and mixtures thereof.

Method of Making

The freshening composition can be made in any suitable manner known in the art. All of the ingredients can simply be mixed together. The method of making may include making a concentrated mixture of ingredients and diluting the concentrated mixture by adding the same to a carrier before dispersing the composition into the air or on an inanimate surface. The method of making may include mixing all of the ingredients except for the sulfur-containing pro-perfume and subsequently adding the sulfur-containing pro-perfume to the mixture of other ingredients. The method may also include pre-mixing the sulfur-containing pro-perfume with some ingredients, such as the solubilizer, polyol, and/or buffering agent before mixing with the other ingredients of the composition.

Freshening Product

The freshening composition can be packaged in any suitable package to form a freshening product. The package may be in the form of a spray dispenser.

The spray dispenser may be transparent or translucent such that the freshening composition is visible or at least partially visible from outside of the freshening product.

The spray dispenser may be comprised of various materials, including plastic, metal, glass, or combinations thereof. The spray dispenser may be pressurized or unpressurized.

One suitable spray dispenser is a plastic aerosol dispenser. The dispenser may be constructed of polyethylene such as a high density polyethylene; polypropylene; polyethyleneterephthalate ("PET"); vinyl acetate, rubber elastomer, and combinations thereof. The spray dispenser may be made of clear PET.

Another suitable spray dispenser includes a continuous action sprayer, such as FLAIROSOL™ dispenser from Afa Dispensing Group. The FLAIROSOL™ dispenser includes a bag-in-bag or bag-in-can container with a pre-compression spray engine, and aerosol-like pressurization of the freshening composition.

The spray dispenser may hold various amounts of freshening composition.

The spray dispenser may be capable of withstanding internal pressure in the range of about 20 p.s.i.g. to about 140 psig, alternatively about 80 to about 130 p.s.i.g.

The total composition output and the spray droplet/particle size distribution may be selected to support the particulate removal efficacy but avoid a surface wetness problem. Total output is determined by the flow rate of the composition it is released from the spray dispenser. To achieve a spray profile that produces minimal surface wetness, it is desirable to have a low flow rate and small Flow rate is determined by measuring the rate of composition expelled by a container for any 60 seconds period of use. The flow rate of the composition being released from the spray dispenser may be from about 0.0001 grams/second (g/s) to about 2.5 grams/second. Alternatively, the flow rate may be from about 0.001 grams/second to about 1.8 grams/second, or about 0.01 grams/second to about 1.6 grams/second.

The mean particle size of the spray droplets may be in the range of from about 10 m to about 100 μm, alternatively from about 20 μm to about 60 μm. At least some of the spray droplets are sufficiently small in size to be suspended in the air for at least about 10 minutes, and in some cases, for at least about 15 minutes, or at least about 30 minutes.

Small particles can be efficiently created when the spray is dispensed in a wide cone angle. For a given nozzle component and delivery tube, cone angles can be modified by varying the insertion depth of the nozzle in the delivery tube. The cone angle may be greater than about 20 degrees, or greater than about 30 degrees, or greater than about 35 degrees, or greater than about 40 degrees, or greater than about 50 degrees.

The spray dispenser may be configured to spray the composition at an angle that is between an angle that is parallel to the base of the container and an angle that is perpendicular thereto. The desired size of spray droplets can be delivered by other types of spray dispensers that are capable of being set to provide a narrow range of droplet size. Such other spray dispensers include, but are not limited to: foggers, ultrasonic nebulizers, electrostatic sprayers, and spinning disk sprayers.

A pressurized spray dispenser may include a propellant. Various propellants may be used. The propellant may comprise hydrocarbon(s); compressed gas(es), such as nitrogen, carbon dioxide, air; liquefied gas(es) or hydrofluoro olefin ("HFO"); and mixtures thereof. Preferably, the product comprises a propellant selected from the group consisting of compressed gas such as compressed air, compressed nitrogen, and combinations thereof. Propellants listed in the U.S. Federal Register 49 C.F.R. § 1.73.115, Class 2, Division 2.2 are considered acceptable. The propellant may particularly comprise a trans-1,3,3,3-tetrafluoroprop-1-ene, and optionally a CAS number 1645-83-6 gas. Such propellants provide the benefit that they are not flammable, although the freshening compositions are not limited to inflammable propellants. One such propellant is commercially available from Honeywell International of Morristown, N.J. under the trade name HFO-1234ze or GWP-6.

If desired, the propellant may be condensable. By "condensable", it is meant that the propellant transforms from a gaseous state of matter to a liquid state of matter in the spray dispenser and under the pressures encountered in use. Generally, the highest pressure occurs after the spray dispenser is charged with a freshening composition but before that first dispensing of that freshening composition by the user. A condensable propellant provides the benefit of a flatter depressurization curve as the freshening composition is depleted during usage.

The pressurized spray dispenser may be free of a hydrocarbon propellant.

The freshening composition may be delivered from the spray dispenser which includes delivery components including but not limited to a valve to control flow and to seal the freshening composition within the spray dispenser, a button actuator and a nozzle for dispensing the freshening composition to the environment.

The aqueous composition may be contained in a bag-in-can plastic spray dispenser.

The freshening composition may be stable over time. Preferably, the freshening composition is stable for at least one year at ambient temperature, more preferably stable for at least two years at ambient temperature, and most preferably stable for at least three years at ambient temperature.

Preferably the freshening composition has $b^*$ value of less 40, more preferably less than 20, more preferably less than 14, more preferably less than 20, more preferably less than 7, more preferably less than 5, and most preferably less than 1, according to the methodology in the Example section below. Preferably the freshening composition has a change in $b^*$ value, which comparing aged versus initial $b^*$ values, of less than 20, preferably less than 14, preferably less than 5.0, more preferably a change of less than 1, and most preferably a change of less than 0.5.

Methods of Use

The freshening composition can be used by dispersing, e.g., by placing the freshening composition into a dispenser, such as a spray dispenser and spraying an effective amount into the air or onto the desired inanimate surface or article. "Effective amount", when used in connection with the amount of the freshening composition, means an amount sufficient to provide at least about 4 hours, or at least about 6 hours, or at least about 8 hours, or at least about 24 hours of freshness or scent to the treated air, surface, or article, yet not so much as to saturate or create a pool of liquid on an article or surface and so that, when dry, there is no visual deposit readily discernible. Where malodor reducing ingredients are included, "effective amount", when used in connection with the amount of the freshening composition, means an amount that provides the foregoing and also provides neutralization of a malodor to the point that it is not discernible by the human sense of smell, yet not so much as to saturate or create a pool of liquid on an article or surface and so that, when dry, there is no visual deposit readily discernible. Dispersing can be achieved by using a spray device, a roller, a pad, etc.

EXAMPLES

Compositions were formulated as outlined in the Tables 3-6 below to evaluate the impact of the sulfur containing pro-perfume (hereinafter "Active Component") on the stability of the freshening compositions.

The initial color of each composition was first measured and then samples are stored in a sealed glass jar at 50 degrees Celsius for two weeks to simulate accelerated aging. After aging for two weeks, color measurements were taken again. Equivalent Stability for Ambient Conditions can predicted based on Arrhenius Equation and Industry Standard Models such as the ICH Models (International Council for Harmonization of Technical Requirements) per given temperature. In general, 2 weeks at 50° C. has been found to be able to predict about 1 year of aging at ambient temperature; 1 month at 50° C. has been found to be able to predict about 2 years of aging at ambient temperature.

The color of each composition is quantitatively measured via a HunterLab LabScan XE spectrophotometer according to the manufacturers published instruction manual to measure the $L^*a^*b^*$ values. The HunterLab LabScan XE spectrophotometer gives Hunter $L^*$-$a^*$-$b^*$color space readings for each sample. The Hunter $L^*$-$a^*$-$b^*$ color space is organized in a cube form. The $L^*$ axis runs from top to bottom. The maximum value for $L^*$ is 100 and the minimum value is zero, which would be black. The $a^*$ and $b^*$ axes have no specific numerical limits. A positive a* value is red, while a negative a* value is green. For these experiments, we primarily focus on the Hunter b* value, which is a measure of how yellow or blue a sample is. A positive b* value is yellow, while a negative b* value is blue. The more positive a b* value is, the more "yellow" a sample is. Stated another way, as the b* value increases, the darker the color of a sample is (orange, brown, red, etc.). Conversely, the more negative the b* value is, the more blue the sample is (clear, white, blue).

For these experiments, we also compare the Initial b* color values to Aged b* values after 2 weeks for notable change in color. The Aged b* value is the measurement taken after two weeks of aging at 50° C. The bigger the difference from Initial b* to Aged b*, the more unstable the sample is, and conversely, the smaller the difference from Initial b* to Aged b*, the more stable the product is.

The same perfume mixture is used in the compositions of Tables 2, 4, and 5 (further referred to as "Perfume Mixture 1") and contains unstable perfume raw materials including: helional, canthoxal, vanillin, ethyl vanillin, beta ionone, dimethyl anthranilate and citral and is combined with several other perfume raw materials.

Experiment 1: Observed Composition Stability Improvement with Active Component

The first set of experiments demonstrates stability improvement with the Active Component when typically unstable perfume mixture is incorporated into aqueous composition containing an acidic buffer and other ingredients as listed in the Table 2 below.

TABLE 2

| Ingredients | Control Compositions Without and With Active Component | | Compositions Comprising Unstable Perfume Mixture Without and With Active Component | |
|---|---|---|---|---|
| | Composition | | | |
| | A | B | C | D |
| Sulfur Containing Pro-perfume (Dodecyl Thio-Damascone) | | 0.06 | | 0.06 |
| Perfume Mixture 1 | | | 0.64 | 0.64 |
| Surfactant (Ethoxylated Hydrogenated Castor Oil) | 1.5 | 1.5 | 1.5 | 1.5 |
| Citric Acid | 0.09 | 0.09 | 0.09 | 0.09 |
| Sodium Citrate | 0.3 | 0.3 | 0.3 | 0.3 |
| Other Ingredients* | 5.36 | 5.36 | 5.36 | 5.36 |
| Deionized Water | To 100 | To 100 | To 100 | To 100 |
| pH Range | 4.5-5.5 | 4.5-5.5 | 4.5-5.5 | 4.5-5.5 |

*Other ingredients include Wetting Surfactant, Preservative, Alcohol and Cyclodextrin and are identical for all the Compositions in Table 2 and 3

As indicated in FIG. 1, Composition A is very stable with negligible color change from Initial and Aged b* values. Composition B is also very stable with negligible color change, demonstrating that the Active Component has no additional effect on the stability of the control composition. Comparing Composition C to Composition A, it is shown in FIG. 1 that the Unstable Perfume Mixture causes Composition C to be unstable with notable change from Initial to Aged b* values. Composition D shows clear stability improvement in Initial and Aged b* values over Composition C, demonstrating the stability improvement resulting from the presence of the Active Component.

Experiment 2: Observed Composition Stability Improvement with Active Component and Unstable Aldehyde Perfume Raw Materials The Second set of experiments demonstrates stability improvement with the Active Component when typically unstable aldehyde perfume raw materials are individually incorporated into aqueous composition containing an acidic buffer and other ingredients as listed in the Table 3 below.

TABLE 3

| | Composition Comprising Helional | | Composition Comprising Canthoxal | |
|---|---|---|---|---|
| | Composition | | | |
| Ingredients | E | F | G | H |
| Dodecyl Thio-Damascone (Haloscent D) | | 0.06 | | 0.06 |
| Helional [3-(1,3-Benzo-dioxol-5-yl)-2-methylpropanal] | 0.3 | 0.3 | | |
| Canthoxal | | | 0.3 | 0.3 |
| Basophor Surfactant (Ethoxylated Hydrogenated Castor Oil) | 1.5 | 1.5 | 1.5 | 1.5 |
| Citric Acid | 0.2 | 0.2 | 0.2 | 0.2 |
| Sodium Citrate | 0.3 | 0.3 | 0.3 | 0.3 |
| Other Ingredients* | 5.36 | 5.36 | 5.36 | 5.36 |
| Deionized Water | To 100 | To 100 | To 100 | To 100 |
| pH Range | 4.5-5.5 | 4.5-5.5 | 4.5-5.5 | 4.5-5.5 |

*Other ingredients include Wetting Surfactant, Preservative, Alcohol and Cyclodextrin and are identical for all the Compositions in Table 2 and 3

Figure 2:
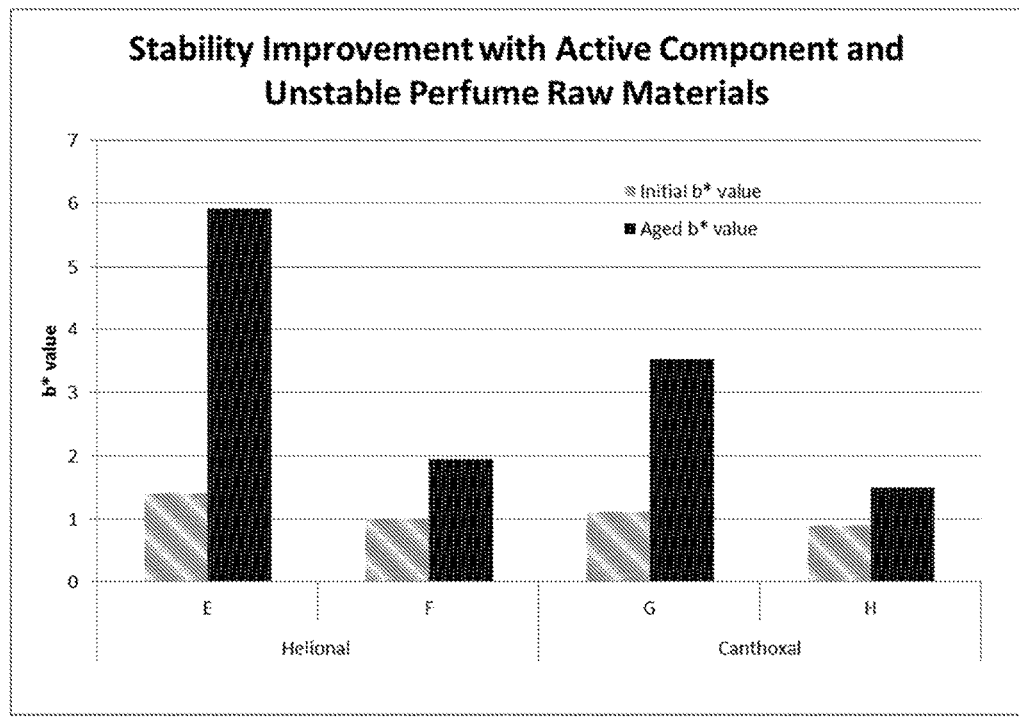
FIG. 2 is a plot of the initial and Aged b* values of Compositions E-H.

As indicated in the FIG. 2, Composition E becomes unstable with notable change from Initial to Aged b* values with the incorporation of Helional, an Aldehyde Perfume Raw Material that is typically unstable when incorporated in aqueous compositions. Comparing Composition E to Composition F, a clear stability improvement resulting from the presence of the Active Component is shown, as composition F shows less change from Initial to Aged b* values. Also shown in FIG. 2, Composition G becomes unstable with notable change from Initial to Aged b* values with the incorporation of Canthoxal, another Aldehyde Perfume Raw Material that is typically unstable when incorporated in aqueous compositions. Comparing Composition G to Composition H, a clear stability improvement resulting from the presence of the Active Component is shown, as composition H shows less change from initial to Aged b* values.

Experiment 3: Observation that Stability Benefit of Sulfur Containing Pro-Perfume Catalyzed by Acidic Environment The third set of experiments listed in Tables 4 and Table 5 and FIG. 3 demonstrates stability improvement of different types on compositions.

TABLE 4

| Composition | pH Range 4.5-5.5 | | pH Range 5.6-6.5 | | pH Range 6.6-7.5 | |
|---|---|---|---|---|---|---|
| | I | J | K | L | M | N |
| Sulfur Containing Pro-perfume (Dodecyl Thio-Damascone) | | 0.06 | | 0.06 | | 0.06 |
| Perfume Mixture 1 | 0.64 | 0.64 | 0.64 | 0.64 | 0.64 | 0.64 |
| Surfactant (Ethoxylated Hydrogenated Castor Oil) | 1.5 | 1.5 | 1.5 | 1.5 | 1.5 | 1.5 |
| Citric Acid | 0.09 | 0.09 | | | | |
| Triethanolamine | | | | | | |
| Monoethanolamine | | | | | | |
| Sodium Citrate | 0.3 | 0.3 | | | | |
| Sodium Polyacrylic Acid | | | 0.1 | 0.1 | | |
| Maleic acid | | | | | 0.06 | 0.06 |
| Sodium Hydroxide | | | | | 0.02 | 0.02 |
| Quaternary Ammonium Compound | | | | | 0.06 | 0.06 |
| Diethylene Glycol | | | | | 0.2 | 0.2 |
| Cyclodextrin | 0.15 | 0.15 | 0.15 | 0.15 | 0.6 | 0.6 |
| Other Surfactants | 0.2 | 0.2 | 0.2 | 0.2 | 0.2 | 0.2 |
| Preservative | 0.01 | 0.01 | 0.01 | 0.01 | 0.01 | 0.01 |
| Alcohol | 5.0 | 5.0 | 5.0 | 5.0 | 3.0 | 3.0 |
| Deionized Water | To 100 | To 100 | To 100 | To 100 | To 100 | To 100 |

TABLE 5

| Composition | pH Range 7.6-8.5 | | pH Range 8.6-9.5 | |
|---|---|---|---|---|
| | O | P | Q | R |
| Sulfur Containing Pro-perfume (Dodecyl Thio-Damascone) | | 0.06 | | 0.06 |
| Perfume Mixture 1 | 0.64 | 0.64 | 0.64 | 0.64 |
| Surfactant (Ethoxylated Hydrogenated Castor Oil) | 1.5 | 1.5 | 1.5 | 1.5 |
| Citric Acid | 0.025 | 0.025 | 0.09 | 0.09 |
| Triethanolamine | 0.10 | 0.10 | | |
| Monoethanolamine | | | 0.10 | 0.10 |
| Sodium Citrate | | | | |
| Sodium Polyacrylic Acid | | | | |
| Maleic acid | | | | |
| Sodium Hydroxide | | | | |
| Quaternary Ammonium Compound | | | | |
| Diethylene Glycol | | | | |
| Cyclodextrin | 0.15 | 0.15 | 0.15 | 0.15 |
| Other Surfactants | 0.2 | 0.2 | 0.2 | 0.2 |
| Preservative | 0.01 | 0.01 | 0.01 | 0.01 |
| Alcohol | 5.0 | 5.0 | 5.0 | 5.0 |
| Deionized Water | To 100 | To 100 | To 100 | To 100 |

Figure 3:
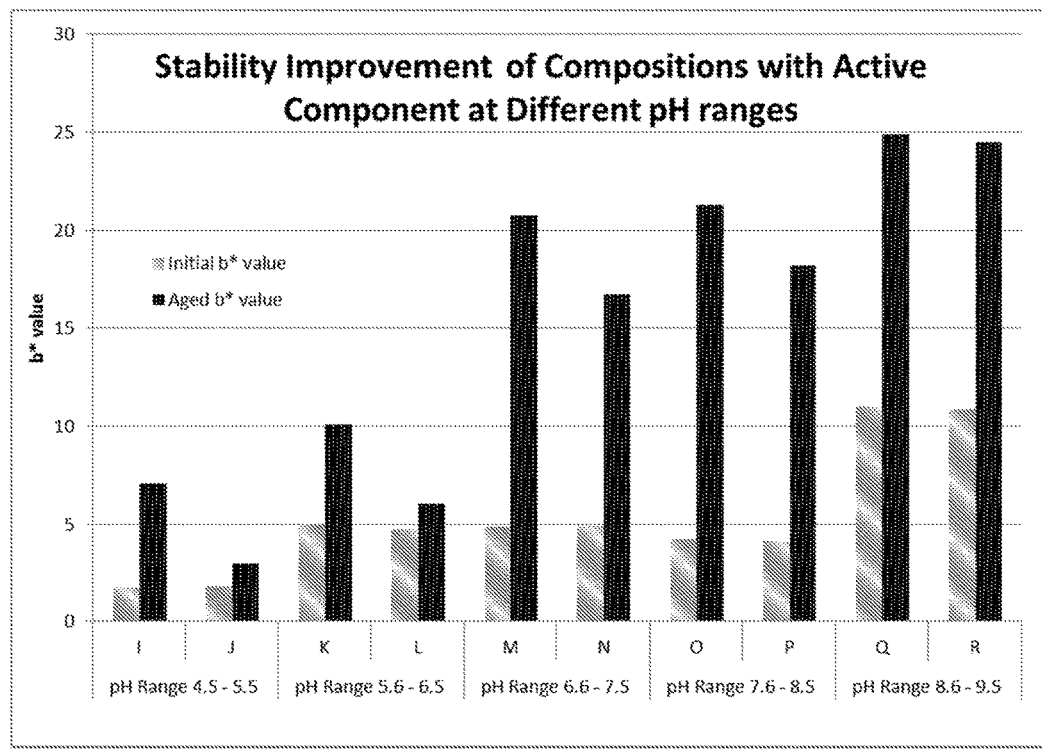
FIG. 3 is a plot of the initial and Aged b* values of Compositions I-R.

As indicated in FIG. 3, the magnitude of stability improvement with Active Component is dependent on formulation environment. The benefit of the Active Component is shown in compositions J, L, N and P compared to compositions I, K, M and O, respectively. Overall b* values are lower in acidic environment and stability improvement with Active Component is enhanced in acidic environment as shown in compositions L and J. Stability improvement with the Active Component is still present in composition N and P even though overall b* values are higher. As shown in compositions R and Q, as compared to compositions I through P, the formulation environment indicated by the pH range 8.5-9.5 can negate stability contributions of the Active Component.

All percentages stated herein are by weight unless otherwise specified. It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments have been illustrated and described, it would be obvious to those skilled in the art that various other changes and modifications can be made without departing from the spirit and scope of the invention. It is therefore intended to cover in the appended claims all such changes and modifications that are within the scope of this invention

What is claimed is:

1. A freshening composition comprising:
    about 0.02 wt. % to about 0.5 wt. %, based on the weight of the composition, of a sulfur-containing pro-perfume, wherein the sulfur-containing pro-perfume is a dodecyl thio-damascone;
    about 0.2 wt. % to about 1.4 wt. %, based on the weight of the composition, of a perfume mixture, the perfume mixture comprising at least one perfume material selected from the group consisting of: 3-(1,3-Benzodioxol-5-yl)-2-methylpropanal, canthoxal, vanillin, ethyl vanillin, citral, and combinations thereof; and
    a carrier, wherein the freshening composition comprises a pH in the range of about 3 to about 8.5.

2. The freshening composition of claim 1 further comprising a carboxylic acid.

3. The freshening composition of claim 2 further comprising a secondary or tertiary amine, wherein the freshening composition comprises a weight ratio of carboxylic acid to secondary or tertiary amine of equal to or greater than 3:1.

4. The freshening composition of claim 1, wherein the freshening composition comprises a weight ratio of perfume mixture to sulfur-containing pro-perfume of about 3:1 to about 35:1, by weight of the freshening composition.

5. A product comprising the freshening composition of claim 1, wherein the product comprises a compressed gas or hydrocarbon propellant.

6. The product of claim 5, wherein the freshening composition is contained in a transparent or translucent spray dispenser.

7. A product comprising the freshening composition of claim 1, wherein the freshening composition is contained in a plastic spray dispenser.

8. The freshening composition of claim 1, wherein the freshening composition is an aqueous composition.

9. The freshening composition of claim 1, wherein the freshening composition is free of primary amines.

10. The freshening composition of claim 1, wherein the perfume mixture further comprises dimethyl anthranilate.

* * * * *